United States Patent [19]
Diessel et al.

[11] Patent Number: 5,837,200
[45] Date of Patent: Nov. 17, 1998

[54] SORTING DEVICE FOR BIOLOGICAL CELLS OR VIRUSES

[75] Inventors: Edgar Diessel, Köln; Walter Weichel, Odenthal, both of Germany

[73] Assignee: Bayer Aktiengesellschaft, Leverkusen, Germany

[21] Appl. No.: 653,143

[22] Filed: May 24, 1996

[30] Foreign Application Priority Data

Jun. 2, 1995 [DE] Germany ................. 195 20 298.8

[51] Int. Cl.$^6$ ................................. G01N 33/00
[52] U.S. Cl. .................. 422/73; 422/58; 422/82.05; 422/82.08; 435/808; 435/288.7; 209/3.1; 209/567; 209/576; 209/155; 209/906
[58] Field of Search ............... 422/55, 58, 68.1, 422/73, 81, 82, 82.05, 82.08; 436/52, 53, 63, 149, 150, 164, 165, 172; 435/5, 29, 30, 34, 808, 288.7; 209/3.1, 552, 567, 576, 606, 906, 132, 155

[56] References Cited

U.S. PATENT DOCUMENTS

| | | | |
|---|---|---|---|
| 4,710,472 | 12/1987 | Saur et al. | 435/308.1 |
| 4,743,361 | 5/1988 | Schram | 209/1 |
| 4,756,427 | 7/1988 | Gohde et al. | 209/3.1 |
| 4,910,148 | 3/1990 | Sorensen et al. | 435/317.1 |
| 5,327,777 | 7/1994 | Kaye et al. | 73/54.06 |
| 5,340,749 | 8/1994 | Fujiwara et al. | 435/526 |
| 5,411,863 | 5/1995 | Miltenyi | 435/6 |
| 5,427,663 | 6/1995 | Austin et al. | 204/549 |
| 5,489,506 | 2/1996 | Crane | 435/2 |

FOREIGN PATENT DOCUMENTS

| | | |
|---|---|---|
| 0177718 | 4/1986 | European Pat. Off. . |
| 0412431 | 2/1991 | European Pat. Off. . |
| 0442025 | 8/1991 | European Pat. Off. . |
| 0581673 | 2/1994 | European Pat. Off. . |
| 1598634 | 4/1971 | Germany . |
| 3310665 | 10/1983 | Germany . |
| 3310551 | 9/1984 | Germany . |
| 3522365 | 1/1987 | Germany . |
| 3534973 | 4/1987 | Germany . |

(List continued on next page.)

OTHER PUBLICATIONS

DE 3827252 abstract, WPIDS AN #90–052406, Feb. 15, 1990.

J.A. Steinkamp, Rev. Sci. Instrum., vol. 64, No. 12, pp. 3440–3450 (1993).

Patent Abstracts of Japan, vol. 10, No. 252, C–369, abstract of JP 61–81779 (1986).

Patent Abstracts of Japan, vol. 10, No. 252, C–369, abstract of JP 61–81778 (1986).

Patent Abstracts of Japan, vol. 12, No. 15, C–469, abstract of JP 62–171677 (1988).

*Primary Examiner*—Maureen M. Wallenhorst
*Attorney, Agent, or Firm*—Srpung Kramer Schaefer & Briscoe

[57] ABSTRACT

The sorting device is able to sort biological objects, particularly cells or viruses, in liquids as a function of physically measurable criteria or properties. The sorting apparatus is provided with a feed inlet (1) for the biological liquid which branches into a microstructured system of multi-parallel main channels (3) and sorting modules (4) each with a switch unit for distribution to two different outlet channels (19,20). Inside a sorting module (4), at least one sensor (9,10) is arranged on each main channel, and a sorting actuator (12) controlled by the relevant sensor is arranged on each switch unit (11). Finally, each outlet channel (20) is connected to a collecting channel (6) for the unselected biological cells or viruses, and each outlet channel (19) is connected to a collecting channel (5) for the selected cells or viruses. If the cells or viruses are magnetically marked, it is possible to dispense with the sensor (9,10) on the main channels (3). In that case, the sorting actuators arranged on the switch units are designed as magnetic deflection modules (37,38). In this case, the magnetic deflection modules undertake direct classification or selection as a function of the magnetic properties of the biological objects to be sorted.

10 Claims, 5 Drawing Sheets

FOREIGN PATENT DOCUMENTS

| | | |
|---|---|---|
| 3712862 | 11/1987 | Germany . |
| 3808798 | 10/1988 | Germany . |
| 3827252 | 2/1990 | Germany . |
| 3840462 | 6/1990 | Germany . |
| 3902402 | 6/1990 | Germany . |
| 3926462 | 2/1991 | Germany . |
| WO 85/01892 | 5/1985 | WIPO . |
| 8505684 | 12/1985 | WIPO . |
| 9115750 | 10/1991 | WIPO . |
| 9216829 | 10/1992 | WIPO . |
| WO 94/28119 | 12/1994 | WIPO . |
| WO 94/29707 | 12/1994 | WIPO . |

SORTING DEVICE FOR BIOLOGICAL CELLS OR VIRUSES

The invention relates to a sorting apparatus for individual biological objects in a liquid for use in biotechnology. The sorting apparatus is based on the principle that the objects are classified directly or indirectly in terms of their physical properties with the aid of suitable sensors. The objects may also be marked in a significant manner for classification. A sorting actuator arranged on a switch unit is then able to distribute the classified biological objects to spatially separated outlet channels. In the case of indirect classification, the sorting actuator is controlled by the sensor assigned thereto as a function of the signal intensity of the sensor. Suitable sensors are primarily fluorescence sensors. The term "biological objects" within the scope of the present application means mainly (living) biological cells.

BACKGROUND OF THE INVENTION

Devices for fluorescence-activated cell sorting (FACS) are obtainable commercially. The sorting principles may be divided into fluidic methods and droplet-oriented systems. With both methods, the cells to be examined are isolated by a coating fluid so that they may be measured individually by fluorescence spectroscopy or by detection of the scattered light.

In the first case, the dispersion to be examined of the cells under examination is conveyed in a liquid jet which is split on the basis of a fluorescence signal into a branch of cell streams which are not to be sorted and a branch of cell streams which are to be sorted. In this case, the flow may be influenced accordingly by a piezoelectric transducer or an ultrasonic transducer.

The most widely used method is that of sorting individual droplets. With this principle, a cell stream emerges through a nozzle. On account of a defined mechanical vibration of the nozzle, the liquid jet breaks up into droplets at a well-defined distance beneath the measuring point, said droplets each bearing at most one cell. Depending on the threshold intensity, a sorting process is initiated in that the liquid jet becomes electrostatically charged by means of the coating fluid. If a charged droplet with the cell to be sorted is broken away from the liquid jet, the liquid jet momentarily loses its charge again with the result that the following droplets do not become charged. Consequently, only the droplet with the cell to be selected remains charged. The drops now fly through the deflecting field of a capacitor. The charged droplet with the cell to be sorted is deflected accordingly and lands in a sorting vessel, whilst the drops which are not to be sorted fly straight ahead into another vessel.

In contrast to the fluidic sorter, higher sorting rates are achieved with the droplet sorter. It is capable of processing approx. $10^8$ cells per day. It must be expected, however, that only 80% of the cells to be selected can actually be sorted in this case. In the case of very rare events in a cell population, however, higher throughputs of approx. $10^{10}$ cells are desirable.

Moreover, a magnetic process is known (MACS= magnetic activated cell sorter) which is obtainable commercially for separating large cell populations. This sorting method utilises the binding of the relevant cells to magnetic beads. In the separation stage, the cells marked in this way are retained in the MACS column by a non-homogeneous magnetic field, whilst the unmarked cells pass unimpeded through the column. However, this process is able to distinguish only between magnetic and non-magnetic cells.

The object of the invention is to separate individual biological objects spatially on the basis of magnetic marking or on the basis of a classification by properties that can be detected by measurement, wherein the cell throughput is to be significantly improved.

SUMMARY OF THE INVENTION

The starting point is a sorting device with the following features in principle:
i) The liquid with the biological objects to be sorted flows via a feed inlet through a main channel on which is arranged a switch unit with at least two outlet channels A, B.
ii) At least one sensor may be arranged on the main channel for the detection and classification of non-magnetically marked cells.
iii) A sorting device is arranged on the switch unit which subsequently distributes the magnetically marked and classified cells selectively to the outlet channels A, B.

DETAILED DESCRIPTION OF THE INVENTION

The above-mentioned object of the invention is achieved in the case of magnetically marked cells in that
a) the feed inlet branches into a microstructured system of multi-parallel main channels and sorting modules each with a switch unit for distribution to two different outlet channels A, B;
b) inside a sorting module, a magnetic deflection module serving as the sorting actuator is arranged on each main channel;
c) and each outlet channel B is connected to a collecting channel for the unselected cells and each outlet channel A is connected to a collecting channel for the selected cells.

An alternative solution which may also be used in the case of non-magnetically marked objects and wherein the objects are optionally marked optically beforehand consists, according to the invention, in the fact that
a) the feed inlet branches into a microstructured system of multi-parallel main channels and sorting modules each with a switch unit for distribution to two different outlet channels A, B,
b) inside a sorting module, at least one sensor is arranged on each main channel, and a sorting actuator controlled by the sensor in question is arranged on each switch unit,
c) and each outlet channel B is connected to a collecting channel for the unselected cells and each outlet channel A is connected to a collecting channel for the selected cells.

Advantageously, an optical sensor for determining the cell size is arranged on each main channel. The optical sensors arranged on the main channels are expediently connected to an external light source via a light guide. Fluorescence sensors are used advantageously as optical sensors.

According to a preferred embodiment, the microstructured system including the optical sensors and the sorting actuators is integrated in a monolithic block, wherein the monolithic block contains preferably 200 to 1000 sorting modules and the internal diameter of the channels is 5 μm to 60 μm.

A particularly advantageous arrangement is one wherein all the elements of the microstructured system including the control electronics is integrated photolithographically in a silicon chip.

According to a further development and completion of the apparatus, the sorting modules are connected to a common external computer which presets the threshold value and the maximum value for selecting the cells.

The sorting actuators to be used for controlling the biological liquid streams may be piezoelectric, magnetostrictive, fluidic or ultrasonic components.

On the basis of the invention, and with the aid of methods from microsystems technology using the well known principle of "measure-decide-sort", a cell sorting apparatus may be produced, the performance of which is increased by at least two orders of magnitude compared with conventional cell sorting apparatus, which represents a significant advance in solving the problem of cell sorting. For example, $10^{10}$ cells may be processed within 24 hours compared with $10^8$ cells in conventional devices. In view of the fact that the sorting apparatus is produced with the aid of microsystems technology, the manufacturing costs of such a device in correspondingly high numbers may be markedly reduced.

BRIEF DESCRIPTION OF THE DRAWINGS

The microsystems-based sorting apparatus according to the invention may be used for screening transfections and cell libraries, for enriching high producers in the case of prokaryotes and eukaryotes, and optionally in medical technology for enriching bone marrow parent cells.

The invention will be explained in more detail below on the basis of drawings and examples.

Figure 1:
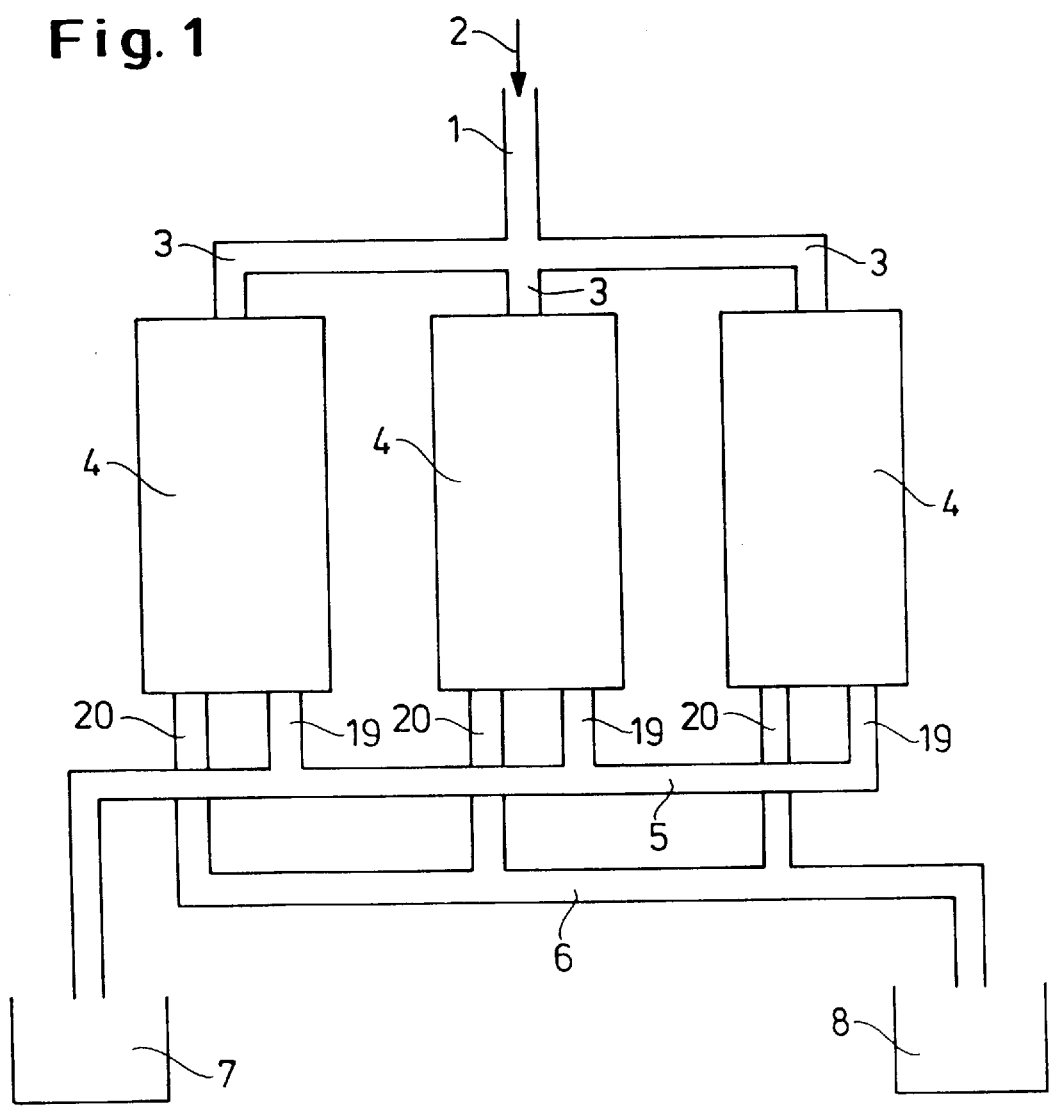
FIG. 1 is a schematic drawing of the structure of the new sorting device

In the sorting device shown schematically in FIG. 1, the cell stream 2 to be sorted flowing through feed inlet 1 is distributed via main channels 3 to individual sorting modules 4 which process the individual partial streams in parallel independently of one another. The main channels 3 are designed as microchannels with a diameter and channel diameter of 7 $\mu$m. After sorting, the streams of the positive and negative channels from each individual module 4 unite to form one collecting channel 5 of the positive cells and one collecting channel 6 of the negative cells. The positive cells are collected in the collecting vessel 7, the negative cells in vessel 8. Due to the multi-parallel operation of a large number of such units, preferably >100, in a so-called sorter array, a substantial increase in the throughput may be achieved.

Figure 2:
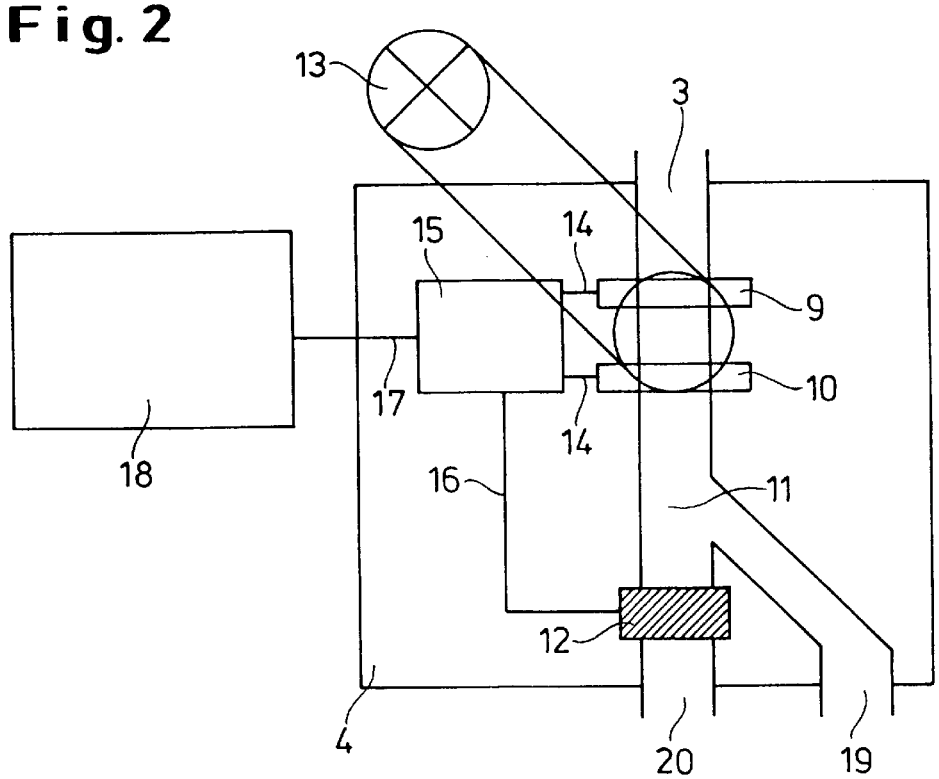
FIG. 2 shows the structure in principle of a sorting module

The structure of the individual sorting module 4 of the sorter array is shown in FIG. 2. It comprises here in each case a main channel 3 with a scattered light sensor 9, a fluorescence sensor 10 and a switch unit 11 arranged downstream of the sensors with a sorting actuator 12. The cells to be sorted are classified with the scattered light sensor according to their geometric size, on the one hand to suppress interference signals, and on the other hand to provide a sorting parameter. The effect utilised here is the size-dependent light scattering of the cells at the wavelength of the excitation light. This principle is also used in conventional FACS. The fluorescence intensity as the main parameter is detected by the optical detector 10. The detectors 9 and 10, optionally in combination with optical filters, are arranged beneath the main channel 3. The excitation light is introduced via light guides from illumination device 13 arranged outside.

The detectors 9 and 10 are connected via lines 14 to evaluation and control electronics 15 which is connected via line 16 to the sorting actuator 12 and via line 17 to an external computer 18. The entire electronics 15 comprises an amplifying part for the measuring signal e.g. with field effect transistors and a control part. Memory, logic elements such as, e.g. comparators and modules for data communication are used in the control part. The main channel 3 with the switch unit 11, the optical sensors 9 and 10, the sorting actuator 12 and the evaluation and control electronics 15, including the electrical leads 14, 16, 17, are integrated on a monolithic silicon chip. The entire electronics part 15 is designed as an ASIC (application-specific integrated circuit) on the Si chip. The electrical connections 14 integrated on the chip provide the control electronics 15 with the information for operating the sorting actuator 12, e.g. a piezoelement. Data processing takes place in parallel in each individual module. Only the sorting criteria are preset by the external computer 18 for all the modules together. Relative threshold values are taken as a basis for the sorting criterion in this case. For example, sorting actuator 12 brings about a diversion of cell flow to the leg or outlet channel 19 of switch unit 11 if the measuring signal is >20% and <80% of the theoretical value set as the fluorescence mean. Outside sorting module 4, the branching leg or outlet channel 19 of switch unit 11 is connected to the collecting channel 5 and the straight leg or outlet channel 20 is connected to the collecting channel 6 (see FIG. 1).

In a similar manner to known cell sorting apparatus, therefore, the cell flow in the case of a positive sorting decision is influenced in such a way that the cells to be sorted flow out into the leg/outlet channel 19 and hence into the collecting channel 5, whilst the remaining cells leave the module through the outlet channel 20 and are fed to the other collecting channel 6 (see also FIG. 1). In a parallel arrangement of approx. 1000 individual modules 4, the throughput and hence the yield may be increased by several orders of magnitude during the cell sorting operation.

Figure 3A:
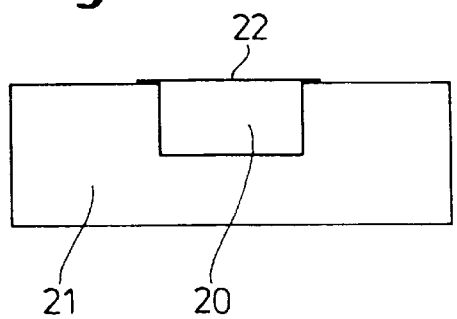
FIG. 3a and 3b shows the operating principle of a piezoelectric sorting actuator
Figure 3B:
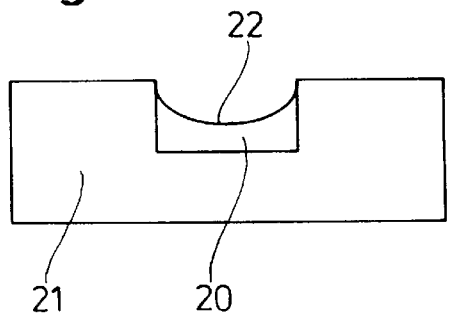

A number of actuator principles are suitable for the sorting actuator which influences the flow of the cell dispersion in the manner described above. Initially, processes will be described on the basis of FIG. 3a and 3b which lead to a narrowing of the channel or leg cross-section 20. FIGS. 3a and 3b show a cross-section through the Si base material 22 with the outlet channel 20. Arranged above the outlet channel 20 is a channel-narrowing actuator 22 in the form of a leaf spring which is in the relaxed state in FIG. 3a and in the activated state in FIG. 3b. An actuator of this kind may be designed as a piezoelement. The use of the piezoelectric deflection principle for cell sorters is already known. By applying a voltage to such an element, the leaf spring will be bent to a greater or lesser extent. Polysilicon is a suitable material which has already been described as a component of a piezoresistive pressure sensor. Piezoelectric actuators based on lithium niobate are also known. Moreover, ultrasonic sensors have been used to influence cell streams.

Figure 4:
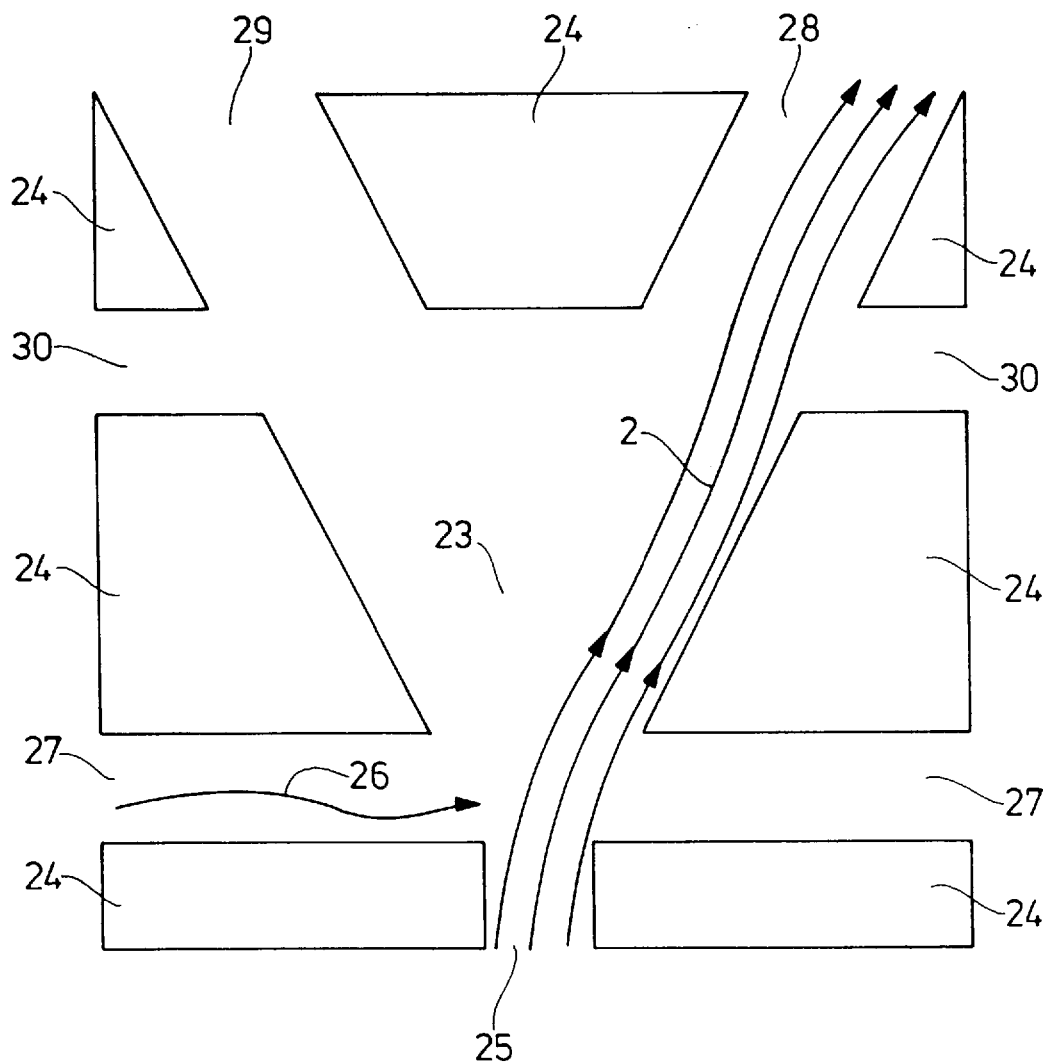
FIG. 4 shows the operating principle of a fluidic sorting actuator

An equivalent effect may also be obtained by means of a thermomechanical actuator. In this case, a silicon spring structure is arched so that the flow of the cell dispersion may in turn be influenced on the basis of a channel narrowing. Moreover, flexible tongues are known which bend under the influence of an external magnetic field due to magnetostrictive forces and in this way may narrow the cross-section of the channel. Moreover, fluidic elements in which small flows of liquid control large streams of liquid should also be able to achieve the required object. A sorting actuator operating on this principle is shown schematically in FIG. 4. The channels 23 with walls 24 that limit the liquid streams are situated in a microstructured base material. The cell dispersion 2 enters the sorting module through an inlet nozzle 25 and in so doing is influenced laterally by a small liquid control stream 26. Said control stream, which flows, for example, from left to right through inlet aperutres 27, causes the cell stream 2 to cling to the right hand side due to the Coanda effect and hence to leave the sorting module through the outlet aperture 28. If the control stream is flowing in the opposite direction, the situation will be laterally reversed and the main stream would leave the module through aperture 29. The equalising apertures 30 serve to equalise the pressures in the module.

Figure 5A:
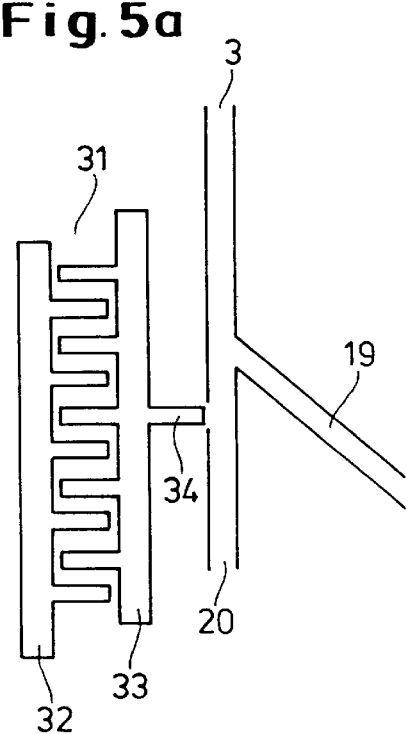
FIG. 5a and 5b shows a sorting actuator with an electrostatic drive
Figure 5B:
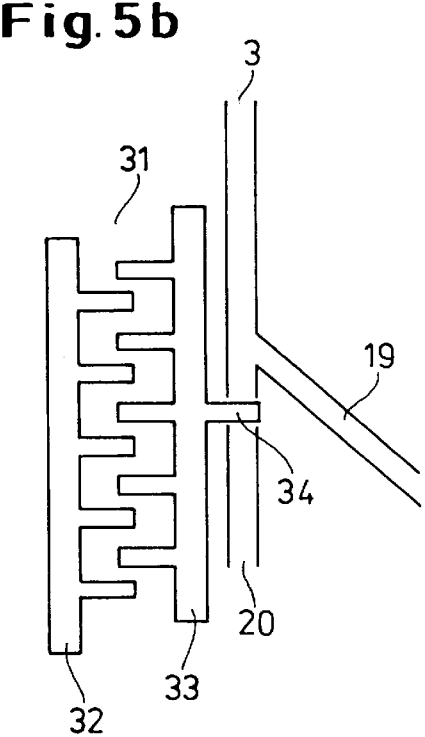

Moreover, sorting actuators based on slide-controlled valves may be used. One such electromechanically operated sorting actuator is shown in FIG. 5a and 5b. It comprises a plate capacitor 31 with a fixed plate 32 and a movable plate 33. Arranged on the movable plate 33 is a valve slide 34 which is able to close the channel cross-section of the outlet channel 20 of switch unit 11. In this way, the flow of the cell dispersion in the sorting module and in the outlet channel 20 can be influenced selectively as a function of the voltage applied. FIG. 5a shows a situation in which the cell dispersion flowing through the main channel 3 emerges undisturbed through the outlet channel 20. In the case of a positive sorting decision, the valve slide 34 according to FIG. 5b is inserted in channel 20 so that the dispersion is deflected in to the other outlet channel 19.

Figure 6:
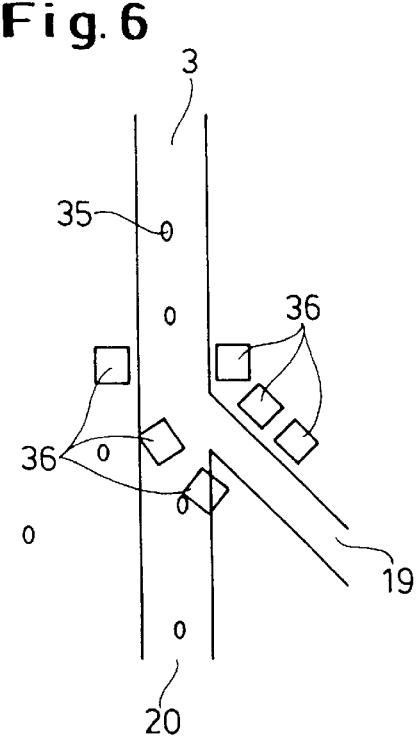
FIG. 6 shows an electromagnetic sorting actuator for magnetically marked cells and FIG. 7 shows a modular sequential arrangement of magnetic and optical sorting modules.

The advantage of separating magnetically marked cells is that a sensor device can be dispensed with, in contrast to fluorescence marking. Accordingly, magnetic marking is used by a magnetic field acting as the actuator as a physical parameter relevant to the sorting process. The magnetic fields of magnetically marked cells required for deflection are produced by planar magnetic coils, the windings of which are composed of e.g. gold. A known magnetic micromotor produced on an Si substrate is based on this principle. A corresponding magnetic deflection module is shown schematically in FIG. 6. The cells 35 enter the module again via main channel 3. Magnetic coils 36 are arranged in a planar fashion along the channel structure, which coils lie optionally on a second plane over the channels. With this arrangement of the coils 36, the deflection path is fixed for the cells 35 which bear magnetic beads as marking and hence leave the module through the outlet channel 19. Magnetically unmarked cells are not deflected by the magnetic fields and therefore pass the module through the other outlet channel 20.

Figure 7:
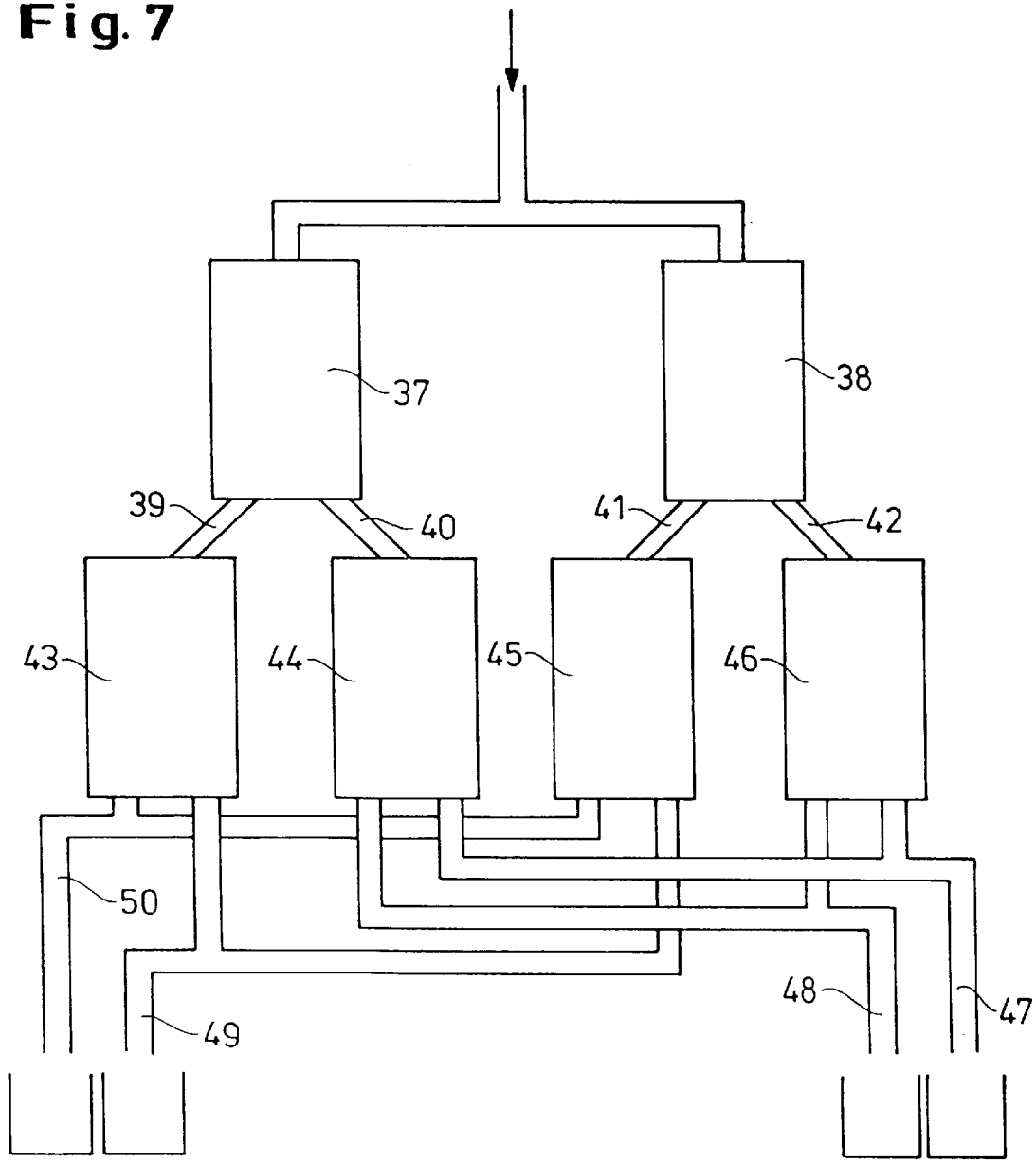

A magnetic sorting module of this kind may also be combined with the optical sorting modules 4 described above in FIG. 1, thus providing an additional sorting parameter. FIG. 7 is a schematic representation of an arrangement for two sorting units arranged in parallel. One unit comprises a magnetic sorting module 37 and 38 (according to FIG. 6) and in each case two optical sorting units 43,44 and 45, 46 connected via the outlet channels 39,40 and 41,42. With this arrangement, the magnetically positive and fluorescence-positive measured cells can be collected in collecting channel 47, the magnetically positive and fluorescence-negative cells in collecting channel 48, the magnetically negative and fluorescence-positive cells in collecting channel 49, and the magnetically negative and fluorescence-negative cells in collecting channel 50.

If operations are carried out only with magnetically marked cells, a magnetic deflection module 37 or 38 may replace the optical sorting module 4 in FIG. 1. As a result of the controlled adjustment of the magnetic fields, the cells may be differentiated according to the number of bound magnetic beads in a cascade arrangement of magnetic deflection units.

The dimensions of a module depend on the size of the cells to be sorted. The diameter of the channels for bacteria is usually 5–10 $\mu$m, and for eukaryotic cells 30–60 $\mu$m. The base material used for the microstructured sorting device is preferably silicon, since both channel structures and optical detection elements (photodiodes) and the control electronics can be integrated monolithically in this case. The conventional methods of semiconductor technology are used in this case, for example, photolithography, ion diffusion, vapour deposition and wet chemical etching.

We claim:

1. A sorting device for biological objects dispersed in liquids, particularly cells or viruses, wherein the objects are magnetically marked in a significant manner for sorting, comprising a feed inlet through which flows a liquid containing magnetically marked and unmarked biological objects, wherein a) the feed inlet branches into a microstructured system of a plurality of main channels which are operated in parallel and simultaneously fed with the liquid, each having a sorting module and two different outlet channels, and each sorting module having a switch unit for distribution of the magnetically marked and unmarked objects to said two different outlet channels, b) each said switch unit comprising a magnetic deflection module as a sorting actuator which distributes the magnetically marked objects selectively to one of said two outlet channels and the magnetically unmarked objects selectively to the other of said two outlet channels, and c) each of said two outlet channels on each main channel is connected to a separate summing channel for the magnetically marked and unmarked objects selectively distributed to it.

2. A sorting device according to claim 1, wherein an optical sensor for determining cell size is arranged on each main channel.

3. A sorting device according to claim 2, wherein the optical sensors arranged on the main channels are connected via light guides to an external light source.

4. A sorting device according to claim 3, wherein at least one optical sensor comprises a fluorescence sensor.

5. A sorting device according to claim 4, further including evaluation and control electronics wherein the microstructured system including the optical sensors, the sorting actuators and the evaluation and control electronics are integrated in a monolithic block.

6. A sorting device according to claim 5, wherein the monolithic block contains 200 to 1000 sorting modules, and in that the internal diameters of the main channels, are each 5 to 60 $\mu$m.

7. A sorting device according to claim 5, wherein all elements of the microstructured system including the evaluation and control electronics are integrated photolithographically in a silicon chip.

8. A sorting device according to claim 1, wherein the sorting modules are connected to a common external computer which presets a threshold value and a maximum value for the distribution of the biological objects.

9. A sorting device according to claim 1, wherein piezoelectric, magnetostrictive, fluidic or ultrasonic components are used as sorting actuators for controlling the liquid flowing through the device.

10. A sorting device for biological objects dispersed in liquids, particularly cells or viruses, wherein the objects are marked in a significant manner of sorting, comprising a feed inlet through which flows a liquid containing marked and unmarked biological objects wherein a) the feed inlet branches into a microstructured system of a plurality of main channels which are operated in parallel and simultaneously fed with the liquid, each having a sorting module and two outlet channels, and each sorting module having a switch unit for distribution of marked and unmarked objects in the liquid said two different outlet channels, b) each said switch unit comprising at least one sensor which detects and classifies the marked objects arranged on each main channel inside a sorting module, and a sorting actuator controlled by each said sensor arranged on each said switch unit, each said sorting actuator distributing the classified marked objects to one of said two outlet channels and the unmarked objects to the other of said two outlet channels, and c) each of said two outlet channels on each main channel is connected to a separate summing channel for the marked and unmarked objects selectively distributed to it.

* * * * *